United States Patent [19]

Morton et al.

[11] Patent Number: 6,099,858
[45] Date of Patent: Aug. 8, 2000

[54] METHODS FOR PREPARING GELATIN CAPSULES CONTAINING FRAGRANCES

[75] Inventors: Frank S. S. Morton, Seminole; Pilar P. Duque, Tampa; Timothy B. Chiprich, St. Petersburg; Norman S. Stroud, Safety Harbor, all of Fla.

[73] Assignee: R. P. Scherer, Troy, Mich.

[21] Appl. No.: 08/935,401

[22] Filed: Sep. 23, 1997

Related U.S. Application Data

[63] Continuation of application No. 08/368,749, Jan. 4, 1995, Pat. No. 5,670,159, which is a continuation of application No. 08/130,589, Oct. 1, 1993, abandoned.

[51] Int. Cl.[7] .................................................... A61K 9/50
[52] U.S. Cl. ............................ 424/456; 264/4.1; 264/4.3; 512/2; 512/4
[58] Field of Search ....................... 424/401, 456, 424/451, 452, 455, 78.03; 514/962; 264/4.1, 4.3; 512/2, 4

[56] References Cited

U.S. PATENT DOCUMENTS

| 4,350,679 | 9/1982 | Mizuno et al. | 424/456 |
| 5,071,706 | 12/1991 | Soper | 424/456 |

*Primary Examiner*—Thurman K. Page
*Assistant Examiner*—R. Bawa
*Attorney, Agent, or Firm*—McDonnell Boehnen Hulbert & Berghoff; Steven J. Sarussi

[57] ABSTRACT

Methods for preparing soft gelatin capsules containing fragrances are disclosed. The desired fragrance is dissolved in a solvent system comprising a volatile solvent, a non-volatile cosolvent, or a combination of a volatile solvent and a non-volatile cosolvent or cosolvents. The resulting mixture is then encapsulated between gelatin ribbions prepared with an odor-free gelatin plasticized with a partially dehydrated, hydrogenated glucose syrup.

11 Claims, No Drawings

METHODS FOR PREPARING GELATIN CAPSULES CONTAINING FRAGRANCES

This is a continuation of application Ser. No. 08/368,749 filed Jan. 4, 1995, now U.S. Pat. No. 670,159; which is a continuation of application Ser. No. 08/130,589 filed Oct. 1, 1993, now abandoned.

BACKGROUND OF THE INVENTION

1. Field of the Invention

This invention relates to novel, single unit or single dose packages comprising fragrances in soft gelatin capsules. This invention also includes within its scope methods for preparing such single application packages and compositions for dispensing fragrances or perfumes in soft gelatin capsules.

2. Description of the Related Art

Fragrances or perfumes are usually prepared from volatile oils distilled or extracted from the leaves, flowers, gums or woods of plant life (occasionally from animal life). These include for example linalyl acetate from citral, jasmine, cedar, lavender and attar of rose. A typical fragrance may consist of many volatile components blended to create a pleasant sensory experience to the person wearing the fragrance and also impart a pleasant sensory experience to the people around that person. These blended oils, however, are typically too potent or too expensive to wear without being diluted in an appropriate solvent. Present perfumeries use lower molecular weight alcohol, e.g. methanol or ethanol, and more typically ethanol, to prepare a variety of "perfume" products such as eau de cologne, perfume, eau de parfum, eau de toilette, splash cologne, and eau fraiche for the consumer.

Distributing samples of perfume to potential customers is a very important practice in the fragrance industry. The methods employed to provide samples of perfume to customers include: glass vials; spray bottles; microencapsulated fragrance adhered to paper; fragrance absorbed onto a polymer matrix enclosed in an aluminum/plastic pouch; fragrance in powder form enclosed in a pouch; and spraying perfume onto blotter cards that are then handed to a customer. Customers are normally presented samples at a store or through the mail.

Each of these methods has drawbacks. For example, glass vials are easily broken and are relatively expensive to make and distribute. In addition, it is difficult and expensive to make vials that will only dispense a single dose of perfume. Spray bottles have been banned by law in some areas. Microencapsulated fragrances adhered to paper typically do not provide a true rendition of the fragrance due to odors of the paper and ink. Fragrances absorbed onto polymer matrices do not have viscosities similar to traditional perfumes. Frequently, rendition of the fragrance is altered when the highly volatile components of the fragrance evaporate from the matrix. Spraying perfume onto a card also alters the rendition. Fragrances in powder form are not readily accepted by comsumers.

Thus, there is a need for a fragrance sample delivery system that is inexpensive to make and distribute, contains only a single dose of the fragrance, is readily accepted by consumers, provides an accurate rendition of the fragrance after storage and distribution with an appearance, feel and viscosity similar to the commercial fragrance. Such a delivery system must allow for simple dispensing of the fragrance.

Soft gelatin capsules generally have a soft shell wall in which the gelatin may be plasticized by the addition of additives such as glycerol, sorbitol or similar polyols. When soft gelatin capsules are filled with ethanol based solutions, however, it has been found that the alcohol, especially when present in concentrations over 5% v/v, diffuses through the capsule wall, thereby shortening the shelf life of the product.

U.S. Pat. Nos. 5,082,661 and 5,063,057 describe the encapsulation of a primary cosmetic composition such as sunscreen, tanning agents, skin anti-wrinkling agents and the like in silicones. U.S. Pat. No. 5,082,661 also suggests the inclusion of other adjunct minor components in addition to the primary cosmetic composition. These minor adjuncts include preservatives, coloring agents, opacifiers and perfumes and may range anywhere from 0.001% up to 20% of the composition. The useful silicones are disclosed as having a broad range of viscosity, i.e., ranging from about 0.5 to 10,000,000 centistokes. It is disclosed that "mixtures of low and high viscosity silicones may be incorporated into the cosmetic formulations."

The Dow Corning Corporation, a manufacturer of silicones, in a bulletin entitled "Dow Corning Formulation Sheet E2-1387A," suggests the use of a single silicone fluid (Dow Corning 344) with Finsolv™-TN/Finetex and isostearyl alcohol as the solvent base in the formulation of a fragrance cologne. Dow Corning also states that other silicone fluids, such as Dow Corning 200, 225, 244, 245 and 345, may be used in perfumes. No suggestion is made by Dow Corning that a fragrance solution comprising a silicone fluid, Finsolv™-TN and isostearyl alcohol may be encapsulated in a soft gelatin capsule.

There are commercial products on the market that use silicones as additives in fragranced skin care and toiletry products such as Giorgio's Red Dry Oil Silkener, and ONE unlimited perfume, La Parfumerie. These products are available in traditional bottles and jars.

The use of ethanol as a solvent for perfumes and fragrances is the standard approach in the industry. Though soft gelatin capsules are generally compatible with fragrances, ethanol tends to migrate through the capsule wall, as discussed above. Therefore, there is a need for a soft gelatin capsule that can successfully contain a fragrance solution without capsule collapse, while at the same time retaining substantially the same or better skin feel and substantially the same or better fragrance rendition as ethanol based perfumes.

SUMMARY OF THE INVENTION

Since ethanol tends to migrate through gelatin capsule walls, substitute solvents for dissolving fragrance oils are needed. Silicone fluids are quite compatible with gelatin and many fragrance oils. However, silicones are sufficiently soluble in glycerol to allow high levels of fragrance migration into the shell of glycerol-plasticized gelatin shells. Because glycerol is infinitely soluble in water, capsules plasticized with glycerol also display unacceptable levels of moisture absorption. Moreover, because traditional or "low Bloom" gelatins have a musky or "animal" odor, capsules prepared with such gelatins give the final fragrance sample an unacceptable odor.

The present invention provides fragrance-containing gelatin capsules that do not utilize substantial amounts of ethanol in the solvent system and, therefore, overcome the deleterious effect previously associated with the use of low molecular weight alcohol solvents. The invention further encompasses methods of dispensing fragrance in soft gelatin capsules that do not employ ethanol. Since the solvent used in the inventive system does not include ethanol, the problems of ethanol induced capsule degradation are avoided.

Broadly speaking, the present invention relates to a single-dose, "unit-of-use" gelatin capsule dosage form for dispensing fragrance without the use of a low molecular weight alcoholic solvent that also avoids the problems associated with glycerol-plasticized shells. The odor of the encapsulated fragrance is retained or improved and at the same time the feel to the skin is superior to an ethanol based solution.

The invention encompasses a soft gelatin shell or capsule containing a fill material which comprises a fragrance dissolved in a fragrance oil-dissolving system, ie., a solvent system. The shells are substantially free from glycerol and are plasticized with a partially dehydrated, hydrogenated glucose syrup. When compared with gelatin capsules prepared with traditional glycerol-plasticized gelatin, the resulting inventive gelatin capsules display (1) dramatically reduced fragrance permeation into the shell, and (2) greatly diminished moisture sensitivity. Thus, the inventive capsules do not collapse or become sticky due to fragrance migration or moisture absorption. In addition, the gelatin shells comprise odor-free, high Bloom gelatins which do not as contribute any odor to the encapsulated perfume sample.

The solvent system is capable of dissolving fragrance-oils and "fine fragrances" of widely differing solubility profiles. The solvent system employed in the present invention comprises (1) a volatile solvent, or (2) a combination of a volatile solvent and a nonvolatile cosolvent or cosolvents. The use of this solvent system results in perfumes that have skin feel and flash off characteristics similar to ethanol based perfumes. The resulting perfumes are non-greasy, light and dry, and soft and spread easily.

Gelatin capsules prepared according to the invention are capable of maintaining and expressing the highly complex and true rendition of the fragrance without any background odor being contributed by either the shell or solvent system. The capsules are readily opened and the encapsulated perfume is simple to dispense. Capsules that are especially simple to open have a tear or twist-off tab portion.

The inventive capsules may be prepared in a variety of shapes and colors. The capsules may be used as a perfume tester or sampler for marketing purposes. In this role, the inventive capsules have numerous advantages as compared to known samplers and testers made from glass, plastics or metal foils. These advantages include improved biodegradability, improved fragrance rendition, improved resistance to breakage, improved barrier to oxidation of the fragrance, reduced allergic reactions for those individuals who are allergic to fragrances, and enhanced shelf life for the product.

DETAILED DESCRIPTION OF THE PREFERRED EMBODIMENTS

As used hereinafter, the term "perfume" means a solution of fragrance while "fragrance" means a neat concentrate, i.e., the scented oil , or blended oils that give the product its characteristic odor. By "fine fragrance" is meant a solution of fragrance in ethanol. A preferred fine fragrance contains from about 5 to 50% fragrance in ethanol.

In accordance with the present invention, there is provided a novel fragrance-containing gelatin capsule and a method of encapsulating fragrance into soft gelatin capsules without the use of a substantial amount of low molecular weight alcoholic solvent or solvents. The gelatin capsules of the invention comprise (a) a substantially odor-free gelatin shell, the shell being substantially free from glycerol and comprising partially dehydrated and hydrogenated glucose syrup; and (b) a fill encapsulated by the shell, the fill comprising fragrance dissolved in a fragrance-dissolving system.

The fragrance-dissolving system, i.e., solvent, typically comprises a volatile solvent and a nonvolatile cosolvent or cosolvents for the fragrance. The gelatin shell is substantially resistant to permeation of the fragrance through the shell. In addition, the capsule has substantially no deleterious effect on the odor produced by the fragrance. The combination of the gelatin shell with the fragrance-dissolving system provides a universal system capable of maintaining the true rendition of a fragrance over an extended storage period and of providing the true fragrance rendition upon opening of the capsule. In other words, the gelatin shell and solvent system cooperate to substantially preserve the rendition of the fragrance to a predetermined age.

The method comprises the steps of (a) forming a solution of a selected fragrance or a blend of fragrances in the solvent system, and (b) encapsulating the solution in a substantially odor-free soft gelatin shell plasticized with a partially dehydrated, hydrogenated glucose syrup.

The rendition of a fragrance, i.e., the odor produced by a fragrance upon application to the skin, is complex and depends upon the specific mixture of various component oils. A fragrance or fine fragrance containing a blend of oils exhibits high, medium and low "notes," each relating to the scent produced by specific oil molecules. High notes result from rapid evaporation of the oils in the fragrance mixture having the highest vapor pressures; those notes are detectable immediately after dispensing a sample of the fragrance. Medium notes are yielded by oils that have lower vapor pressures and evaporate more slowly; they are detectable for 2–3 hours after the fragrance is dispensed. Low notes result from the oils that remain and are detectable after the high and medium notes have completely disappeared. Any change of the composition of the fragrance oils in the fill resulting from migration of fragrance into the shell provides a different and, therefore, unacceptable rendition of the fragrance.

Since certain silicones, in particular DC 245, are soluble in glycerol at about 10% by weight, silicone in capsule fill material migrates into the capsule shell carrying fragrance with it. Thus, capsules having glycerol-plasticized gelatin shells tend to exhibit unacceptable levels of fragrance migration or permeation into the shell. The present invention is a substantially stable or static system i.e., the gelatin shell and fill material together minimize any change in the composition due to permeation into the shell and allow for the expression of the desired fragrance when the capsule is opened. In addition, to diminish any odor contributed by the shell, the inventive capsules are prepared using high-Bloom gelatin.

Because glycerol is infinitely soluble in water, capsules plasticized with glycerol also display unacceptable levels of moisture absorption. Even at relative humidity (RH) levels as low as 30%, capsules prepared with glycerol absorb water, become sticky, and are difficult to open. Gelatin capsules prepared with partially dehydrated, hydrogenated glucose syrup plasticizers that are substantially free from glycerol are suitable for storage for long periods of time in low to moderate humidity conditions and for storage for at least considerable amounts of time in high to very high humidity conditions without becoming sticky or difficult to open.

Gelatin capsules prepared according to the invention are capable of maintaining and expressing the highly complex and true rendition of the fragrance oils without any substantial background odor being contributed by either the shell or solvent system. The capsules are readily opened and the encapsulated perfume is simple to dispense.

The shells of the fragrance-containing capsules are plasticized with a partially dehydrated, hydrogenated glucose syrup. These glucose syrups may be derived from a variety of starch sources. A preferred source is corn. Typically, such syrups comprise from 25 to 40% by weight of sorbitol and from 20 to 30% by weight of sorbitans (the major proportion of the sorbitan component being 1,4-sorbitan) together with water (typically in an amount of 13 to 20% by weight) and other polyhydric alcohols, the mannitol content being from 0 to 6% by weight.

The amount of sorbitol/sorbitan(s) mixture in the dry shell is suitably from 4 to 50% by weight, preferably from 10 to 40% by weight and more preferably from 20 to 30% by weight.

As noted above, the sorbitol/sorbitan(s) mixture may contain other polyhydric alcohols but in this case the total amount of sorbitol and sorbitan(s) in the whole sorbitol/sorbitan(s)/other polyhydric alcohol(s) mixture is suitably from 45 to 75% by weight, preferably from 55 to 66% by weight. The other polyhydric alcohols are suitably hydrogenated saccharides.

The total mixture normally contains not more than 6% by weight of mannitol and preferably contains from 1 to 4% by weight, more preferably from 2 to 3% by weight of mannitol.

A preferred dehydrated, hydrogenated glucose syrup is sold by and is available from Roquette Freres, Letrem, France as Anidrisorb 85/70. This material has the following composition: about 20 to 35% by weight sorbitol; about 15 to 25% by weight sorbitans; about 2 to 6% by weight mannitol; and about 5 to 15% by weight hydrogenated saccharides. When compared with gelatin capsules prepared with traditional glycerol-plasticized gelatin, the resulting inventive gelatin capsules display (1) dramatically reduced fragrance permeation into the shell, and (2) greatly diminished moisture sensitivity. The preferred plasticizers of the invention are substantially free from or low in glycerol.

When stored, fragrance-containing gelatin capsules prepared with traditional low-Bloom gelatin develop odors that detract from the scent of the fragrance encapsulated therein. Traditional or low-Bloom gelatins have Bloom values of from about 120 to 180. Therefore, in preferred embodiments of the invention, the gelatin shell is prepared using odor-free, high-Bloom gelatins. Such gelatins have Bloom values of at least about 220 and typically from about 220 to 300. Examples of odor-free, high-Bloom gelatins are: an inert, deionized and oxidized gelatin; a first extract, partially or fully de-salted, limed bone gelatin; and a blend of first, second and third extract, limed-bone gelatins.

In alternate embodiments, the gelatin shell may be prepared using a low-Bloom gelatin that has been purified or treated in such a fashion as to be substantially odor-free.

The solvent system is capable of dissolving fragrances and "fine fragrances" of widely differing solubility profiles. The solvent system employed in the present invention comprises (1) a volatile solvent, or (2) a combination of a volatile solvent and a nonvolatile cosolvent or cosolvents. The use of this solvent system results in perfumes that have skin feel and flash off characteristics similar to ethanol based perfumes. The resulting perfumes are -non-greasy, light and dry, soft and spread easily.

According to the invention, the volatile solvent may be a volatile silicone or an aliphatic or aromatic hydrocarbon.

The volatile silicone may be single silicone fluid or a blend of two or more miscible silicone fluids. In general, low viscosity silicone fluids are most advantageous having viscosities in the range between about 0.5 and about 10 centistokes at 25° C. However, small amounts of higher viscosity silicones may be used in a blend with low viscosity silicones as long as the viscosity of the resulting partially volatile blend does not greatly exceed 20 cst.

Among the silicone compounds suitable for incorporation into the fill material of the invention are dimethicones and cyclomethicones which may be represented by the formula:

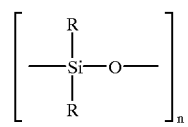

wherein R is a 1 to 3 carbon alkyl group, n is a integer from 3 to 10, preferably from 3 to 7, and the unsatisfied valences on the oxygen and silicon atoms at the ends of the chain may be joined to one another to form a cyclic structure.

Various silicone fluids may be used, for example, dimethicones, cyclomethicones, and substituted siloxanes. Representative silicone fluids are available from Dow Corning and include silicone DC 200 (hexamethyldisiloxane, 0.65 cst), DC 200 (octamethyltrisiloxane, 1.0 cst) DC 244 (predominantly octamethylcyclotetrasiloxane), DC 245 (predominantly decamethylcyclopentasiloxane), DC 344 (cyclopolydimethylsiloxane blend of decamethylcyclopentasiloxane and octamethylcyclotetrasiloxane) and DC 345 (cyclopolydimethylsiloxane blend of dodecamethylcyclohexasiloxane, decamethylcyclopentasiloxane and octamethylcyclotetrasiloxane). A 1.0 cst DC 200 is preferred over a 0.65 cst DC 200.

Typical vapor pressures of silicones are shown in the table below. These vapor pressures were determined using Dow Corning 344 fluid at various temperatures.

| Temperature | Vapor Pressure, mm Hg |
| --- | --- |
| 26° C. | 1 |
| 64° C. | 10 |
| 77° C. | 20 |
| 92° C. | 40 |
| 101° C. | 60 |
| 114° C. | 100 |
| 155° C. | 400 |
| 178° C. | 760 |

The volatile solvent may also be an aliphatic or aromatic hydrocarbon compound. The hydrocarbon is typically a straight or branched chain saturated aliphatic hydrocarbon having from 6 to 25 carbon atoms. Representative hydrocarbons include isododecane (2,2,6,6-tetramethyl-4-methyleneheptane), isohexadecane (2,2,4,4,6,6,8-heptamethylnonane), and isoeicosane. A preferred hydrocarbon, isododecane, is available from Presperse, Inc. South Plainfield, N.J., as Permethyl 99A.

The second component of the solvent system is a nonvolatile cosolvent. The cosolvents suitable for use in the fill materials for the inventive gelatin capsules are various (1) $C_6$–$C_{22}$ straight or branched chain alkyl esters of straight or branched chain carboxylic acids having 8–18 carbon atoms; (2) benzyl or $C_6$–$C_{22}$ straight or branched chain alkyl benzoates; (3) $C_6$–$C_{22}$ straight or branched chain alkyl esters of straight or branched chain carboxylic acids having 8–18 carbon atoms; (4) $C_6$–$C_{22}$ straight or branched chain alkoxyalkyl esters of straight or branched chain carboxylic acids having 8–18 carbon atoms; (5) glyceryl esters containing 8–18 carbon atoms derived from the carboxylic acid; (6) sorbitan esters; (7) straight or branched alkyl esters of alkoxylated fatty acid esters; and (8) fatty alcohols having from 10–22 carbon atoms.

A preferred alkyl benzoate is a $C_{12}$–$C_{15}$ alkyl benzoate available from Finetex (Elmwood Park, N.J.) as Finsolv™ TNO. Finsolv™ TNO is odorless, which, of course, is a desired characteristic of any component of the invention, other than the fragrance. Other preferred cosolvents are benzyl benzoate, PPG-2 myristyl ether propionate (which has the formula: $CH_3(CH_2)_{12}CH_2(OCH(CH_3)CH_2)_2O_2CCH_2CH_3$), isopropyl myristate, isostearyl myristate, and isocetyl alchol.

The volatile solvent ranges from about 0% to about 100% w/w of the solvent or fragrance-dissolving system. A more preferred range for the volatile solvent is from about 30% to about 70% w/w. Yet more preferred amounts of volatile solvent typically lie in the range of from about 50% to 70% w/w of the solvent system. In a most preferred embodiment, the volatile silicone is at least about 55% by weight of the fragrance-dissolving system.

The amount of cosolvent in the system ranges from about 0% to about 100% w/w; more preferably, the amount of cosolvent in the system ranges from about 30% to about 70% w/w. In a most preferred embodiment, the cosolvent or cosolvent mixture is less than about 45% by weight of the fragrance-dissolving system.

In more preferred embodiments of the invention, the cosolvent component comprises a combination of a $C_6$–$C_{22}$ straight or branched chain alkyl benzoate and a fatty alcohol having from 10–22 carbon atoms. Particularly preferred fatty alcohols are isocetyl and isostearyl alcohols. In a most preferred embodiment, the alkyl benzoate is a $C_{12}$–$C_{15}$ alkyl benzoate and the fatty alcohol is isocetyl alcohol. The weight ratio of the $C_{12}$–$C_{15}$ alkyl benzoate to fatty alcohol in the combination cosolvent ranges from about 1:2 to 4:1. In preferred embodiments the weight ratio of alkyl benzoate to fatty alcohol is about 3:2.

A more preferred solvent system according to the invention contains from about 50–60% w/w of a volatile solvent, about 25–30% w/w of an alkyl benzoate, and from about 15–20% w/w of a fatty alcohol. A particularly preferred solvent system comprises from about 22 to 32% by weight of the fragrance-dissolving system of a $C_{12}$–$C_{15}$ alkyl benzoate, and from about 13 to 23% by weight of the fragrance-dissolving system of a fatty alcohol having from 10–22 carbon atoms.

The selected fragrance oil is dissolved in the fragrance-dissolving system described above by mixing in a suitable vessel until dissolution is complete. The resulting product is then filled into a soft gelatin capsule, which is thereafter sealed by known procedures yielding the encapsulated fragrance.

Various conventional methods of making soft gelatin capsules may be used, such as the well known rotary die process. Similarly, various conventional capsule shapes and sizes may be used. A particularly advantageous capsule shape includes a tear or twist off tab portion, such as shown in U.S. Pat. No. 2,134,489. In such a capsule, the encapsulated perfume can be easily accessed by the user by simply twisting or tearing off the tab and applying the perfume to the skin. The fragrance-containing soft gelatin capsules typically contain from about 0.02 ml to about 2ml of a solution of the fragrance in the solvent system, and more preferably about 0.1 ml.

The inventive capsules offer unexpected advantages over fragrance products that utilize an alcoholic solvent. For example, when the inventive product is applied to the skin it exhibits a similar skin feel and evaporation rate as an alcoholic solvent with little or no stinging effect and with little or no greasiness. Also, the use of the solvent base only minimally affects the olfactory rendition of the fragrance dissolved in the solvent.

An effective amount of the fragrance to give the desired odor is used. The level to be blended into the silicone base is determined by the type of perfume to be made (i.e. eau de cologne, perfume, etc.) and the desired effect of the fragrances. Typically from about 5% up to about 40% w/w fragrance may be blended into the solvent base. Preferred compositions of fragrance in solvent system contain about 10%–20% (w/w) fragrance.

In some instances, known additives, such as solubilizers, antioxidants, preservatives, fixative/coupling agents and coloring agents, may be incorporated into the formulation to improve the perfume. Because these additives may not be as volatile as the silicones and may adversely affect the fragrance rendition, their concentration should desirably be kept at a low concentration that does not adversely affect the rendition of the fragrance.

Furthermore, additives that have a deleterious effect on the fragrance or on the skin feel characteristics of the resulting perfume are to be avoided.

The following examples are included to illustrate the practice of this invention.

EXAMPLE 1

A solution of the following composition was made:

| | |
|---|---|
| dimethicone[1] | 37.5% w/w |
| cyclomethicone[2] | 37.5% w/w |
| $C_{12}$–$C_{15}$ alkyl benzoate[3] | 15% w/w |
| Fragrance oil[4] | 10% w/w |

[1]DC 200 (1.0 cst)
[2]DC 245
[3]Finsolv ™ TNO
[4]Tracy (Givaudan-Roure, TAZ 48082)

Precise unit amounts of the solutions prepared above are filled and sealed into soft gelatin capsules with twist off tabs with volumes of about 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall. This gelatin capsule is Formulation 1 in Table I below.

Upon removing the twist off tabs, a precise amount of the encapsulated fragrance solution may be conveniently released on the user's skin. The fragrance rendition of the solution is accurate and the skin feel of the solution is pleasing without undue stinging or greasiness.

TABLE I

| INGREDIENT | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Dimethicone[6] | 37.5 | 80 | 75 | 40 | | | | 45 | 50 | 40 | 45 | 50 | 50 | | |
| Cyclomethicone[7] | 37.5 | | | | 80 | | | | | | | | | | |
| Benzoic Acid ($C_{12}$–$C_{15}$)alkyl ester[8] | 15.0 | 10.0 | 15 | 50 | 10 | 5 | | | | | | 24 | 24 | 24 | |
| Aliphatic hydrocarbon[9] | | | | | | 85 | 15 | | | | 45 | | | 50 | 60 |
| Benzyl benzoate | | | | | | | 75 | | | | | | | | |
| PPG-2 Myristyl ether propionate | | | | | | | | 45 | | | | | | | 30 |
| Iso-propyl myristate | | | | | | | | | 40 | 50 | | | | | |
| Iso-stearyl alcohol | | | | | | | | | | | | 16 | | 16 | |
| Iso-cetyl alcohol | | | | | | | | | | | | | 16 | | |
| Fragrance | 10 | 10 | 10 | 10 | 10 | 10 | 10 | 10 | 10 | 10 | 10 | 10 | 10 | 10 | 10 |

[5]amount of component is given in weight percent of total fill formulation
[6]DC 200 (1.0 cst)
[7]DC 245
[8]Finsolv ™ TNO
[9]Permethyl 99A (isododecane)

EXAMPLE 2

Formulations 2–15 were prepared in essentially the same manner as Formulation 1. These formulations are shown above in Table 1.

EXAMPLE 3

A solution of the following composition was made:

| | |
|---|---|
| silicone DC 200 (1 cst) | 40% w/w |
| $C_{12}$–$C_{15}$ alkyl benzoate | 50% w/w |
| Fragrance oil | 10% w/w |

Unit amounts of the solutions prepared above are filled and sealed into soft gelatin capsules with twist off tabs with volumes of 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall.

EXAMPLE 4

A solution of the following composition was made:

| | |
|---|---|
| silicone DC 200 (1 cst) | 45% w/w |
| PPG-2 ether propionate myristyl (Crodamol PMP) | 45% w/w |
| Fragrance oil | 10% w/w |

Unit amounts of the solutions prepared above are filled and sealed into soft gelatin capsules with twist off tabs with volumes of 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall.

EXAMPLE 5

A solution of the following composition was made:

| | |
|---|---|
| silicone DC 244 | 50% w/w |
| isopropyl myristate | 40% w/w |
| Fragrance oil | 10% w/w |

Unit amounts of the solutions prepared above are filled and sealed into soft gelatin capsules with twist off tabs with volumes of 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall.

EXAMPLE 6

A solution of the following composition was made:

| | |
|---|---|
| isododecane | 50% w/w |
| isostearyl alcohol | 16% w/w |
| $C_{12}$–$C_{15}$ alkyl benzoate | 24% w/w |
| Fragrance oil | 10% w/w |

Unit amounts of the solutions prepared above are filled and sealed into soft gelatin capsules with twist off tabs with volumes of 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall.

EXAMPLE 7

A solution of the following composition was made:

| | |
|---|---|
| silicone DC 245 | 50% w/w |
| isocetyl alcohol | 16% w/w |

-continued

| | |
|---|---|
| $C_{12}$–$C_{15}$ alkyl benzoate[10] | 24% w/w |
| Fragrance oil | 10% w/w |

[10]Finsolv ™ TNO

Unit amounts of the solutions prepared above are filled and sealed into soft gelatin capsules with twist off tabs with volumes of 0.1 ml by the rotary die process. The gelatin ribbons employed were prepared using high-Bloom gelatin plasticized with a partially dehydrated, hydrogenated glucose syrup available as Anidrisorb 85/70. The capsules are then stored at room temperature. No dimpling of the wall is observed indicating that the solution does not diffuse through the gelatin wall.

Upon removing the twist off tabs, a precise amount of the encapsulated fragrance solution may be conveniently released on the user's skin. The fragrance rendition of the solution is accurate and the skin feel of the solution is pleasing without undue stinging or greasiness.

Many other embodiments not specifically disclosed or discussed above may nevertheless fall within the spirit and scope of the present invention and claims.

What we claim is:

1. A method of preparing a fragrance-containing gelatin capsule comprising the steps of:

(a) preparing a fill material containing from about 5–40% of a fragrance based on the weight of the fill material, the fragrance being dissolved in a fragrance-dissolving system comprising a volatile solvent selected from the group consisting of dimethicones, cyclomethicones, substituted siloxanes, aromatic hydrocarbons of about 6 to 30 carbon atoms, and aliphatic hydrocarbons having about 6 to 25 carbon atoms, a nonvolatile cosolvent selected from the group consisting of $C_6$–$C_{22}$ straight or branched chain alkyl esters of straight or branched chain carboxylic acids having 8 to 18 carbon atoms, benzyl or $C_6$–$C_{22}$ straight or branched chain alkyl benzoates, $C_6$–$C_{22}$ straight or branched chain alkyl esters of straight or branched chain carboxylic acids having 8 to 18 carbon atoms, $C_6$–$C_{22}$ straight or branched chain alkoxyalkyl esters of straight or branched chain carboxylic acids having 8 to 18 carbon atoms, glyceryl esters containing 8 to 18 carbon atoms derived from the carboxylic acid, sorbitan esters, straight or branched alkyl esters of alkoxylated fatty acid esters, and fatty alcohols having from 10 to 22 carbon atoms, or mixtures thereof; and (b) preparing a pair of gelatin ribbons comprising a blend of odor-free gelatin having a bloom value of from about 220–300 and a partially dehydrated and hydrogenated glucose syrup comprising at least about 25% by weight of sorbitol, at least about 20% by weight of sorbitans, water and polyhydric alcohols; and (c) encapsulating the fill material within the the ribbons to form a capsule, the capsule having no substantial deleterious effect on the odor produced by the fragrance upon application to the skin.

2. A method according to claim 1 wherein the volatile solvent is at least about 5 to 95% by weight of the fragrance-dissolving system and the cosolvent is less than about 5 to 95% by weight of the fragrance-dissolving system.

3. A method according to claim 2, wherein the volatile solvent is from about 30 to 70% by weight of the fragrance-dissolving system and the cosolvent is from about 30 to 70% by weight of the fragrance-dissolving system.

4. A method according to claim 3, wherein the volatile solvent is at least about 55% by weight of the fragrance-dissolving system and the cosolvent is less than about 45% by weight of the fragrance-dissolving system.

5. A method according to claim 4, wherein the gelatin is a limed bone gelatin.

6. A method according to claim 5, wherein the volatile solvent is a volatile silicone and the cosolvent comprises from about 22 to 32% by weight of the fragrance-dissolving system of a $C_{12}$–$C_{15}$ alkyl benzoate, and from about 13 to 23% by weight of the fragrance-dissolving system of a fatty alcohol having from 10–22 carbon atoms.

7. A method according to claim 6, wherein the fatty alcohol is isocetyl alcohol or isostearyl alcohol.

8. A method according to claim 7, wherein the fragrance is present in the fill as a solution of the fragrance in ethanol.

9. A method according to claim 8, comprising (d) drying the capsule to provide a dried capsule having a shell comprising from about 4–50% by weight of a mixture of sorbitol and/or sorbitans.

10. A method according to claim 8, comprising (d) drying the capsule to provide a dried capsule having a shell comprising from about 10–40% by weight of a mixture of sorbitol and/or sorbitans.

11. A method according to claim 8, comprising (d) drying the capsule to provide a dried capsule having a shell comprising from about 20–30% by weight of a mixture of sorbitol and/or sorbitans.

* * * * *